United States Patent
Iimura

(10) Patent No.: US 6,675,425 B1
(45) Date of Patent: *Jan. 13, 2004

(54) PHOTOCATALYTIC APPARATUS AND METHOD FOR ACTIVATING PHOTOCATALYTIC MATERIAL

(76) Inventor: Keiji Iimura, 10-8, Akatsuka 3-chome, Itabashi-ku, Tokyo 175-0092 (JP)

( * ) Notice: Subject to any disclaimer, the term of this patent is extended or adjusted under 35 U.S.C. 154(b) by 334 days.

This patent is subject to a terminal disclaimer.

(21) Appl. No.: 09/629,478

(22) Filed: Jul. 31, 2000

Related U.S. Application Data

(62) Division of application No. 09/161,013, filed on Sep. 25, 1998, now Pat. No. 6,094,767.

(51) Int. Cl.⁷ .............................................. A46B 15/00
(52) U.S. Cl. .................................... 15/105; 250/504 H
(58) Field of Search ....................... 422/22, 24; 15/105, 15/339; 604/20; 601/15; 250/504 H

(56) References Cited

U.S. PATENT DOCUMENTS 5,919,422 A * 7/1999 Yamanaka et al. ...... 422/122 X
5,921,251 A * 7/1999 Joshi ........................ 132/112
6,094,767 A * 8/2000 Iimura ....................... 15/105

FOREIGN PATENT DOCUMENTS

| EP | 1217056 A1 | * 12/2000 |
| JP | 0690824 A | * 4/1994 |
| WO | WO-98/27891 A1 | * 7/1998 |

* cited by examiner

Primary Examiner—Elizabeth McKane

(57) ABSTRACT

A photocatalyst apparatus includes a substrate; a plurality of photocatalytic fibers, each of the photocatalytic fibers having a core or a sheath covering the core and a plurality of photocatalytic particles dispersed therein; and wherein the photocatalytic fibers are disposed on/in the substrate. Another photocatalyst apparatus includes a substrate having a substantially transparent member and a plurality of light diffusing particles dispersed therein; and a plurality of photocatalytic fibers disposed on/in the substrate, each of the photocatalytic fibers containing a photocatalyst disposed therein/thereon. The photocatalyst apparatus may be applicable to a dental cleaner or toothbrush. A cleaner for cleaning floors, carpets and/or walls, the cleaner includes: a cleaning head including a plurality of brushes containing a photocatalyst disposed hereon/therein; and at least one light source in communication with the photocatalyst. The cleaner may be applicable to a vacuum cleaner.

30 Claims, 14 Drawing Sheets

PHOTOCATALYTIC APPARATUS AND METHOD FOR ACTIVATING PHOTOCATALYTIC MATERIAL

CROSS-REFERENCE TO RELATED APPLICATIONS

This is a division of U.S. patent application Ser. No. 09/161,013, filed on Sep. 25, 1998, entitled "CLEANING APPARATUS USING PHOTOCATALYST", and issued on Aug. 1, 2000, U.S. Pat. No. 6,094,767.

The prior foreign application of the U.S. patent application Ser. No. 09/161,013 is Japanese Patent application No. H08-103131, filed on Mar. 21, 1996, and laid open on Sep. 30, 1997, Publication of unexamined patent application No.253595/1997.

BACKGROUND OF THE INVENTION

1. Field of the Invention

The invention relates to a photocatalytic apparatus including photocatalytic material and a method for activating the photocatalytic material.

2. Description of the Related Art

It is known that a photocatalyst (i.e. photocatalytic material) activating by light rays with relatively short wavelength decomposes or dissolves the organic or inorganic substances, which are undesirable to humans and environments, such as bacteria, molds (i.e. fungus), nicotine, tar, tartar, colored scale, pollutants to cause environmental pollution and etc. When the substances approach to or come in contact with the photocatalyst activated by the light rays, they are subjected to oxidation and/or reduction reactions in order to be decomposed or dissolved by a photocatalyst effect, so that they are rendered harmless.

Typical photocatalyst is a kind of photo-activated semiconductor (i.e. photocatalytic semiconductor) such as titanium dioxide ($TiO_2$).

Multiple photocatalyst particles (i.e. photocatalytic particles) are used as a form of photocatalyst supported substrate, in which a layer (i.e. film) including the photocatalyst particles is fixed and supported on the substrate, a recycling of the photocatalyst particles can be easily done because the separation and collection of the photocatalyst particles are not needed.

For example, the publication of unexamined patent application of Japan No. 155726/1993 discloses that Titanium Dioxide layer of the photocatalyst is coated on a substrate such as metal, ceramic and glass, for the purpose of protecting a surface of the substrate from growth of bacteria.

U.S. Pat. No. 4,526,570 issued on Jul. 2, 1985 to Nakagawa et al. discloses a dental hygienic device for hygienic treatment of teeth in an oral cavity (i.e. toothbrush), which is composed of a n-type semiconductor having a photoelectric effect using photoelectric chemical reaction, in which the semiconductor is disposed on or in a main body consisting of an insertion portion and a handle.

SUMMARY OF THE INVENTION

It is an object of the present invention is to provide a novel photocatalytic apparatus including photocatalytic material.

It is another object of the present invention is to provide a method for activating the photocatalytic material.

A first aspect of the present invention is a photocatalytic apparatus, which includes a substrate, fiber-like members (i.e. fibers, filaments, needles, bristles, whiskers), each of the fiber-like members including photocatalytic material, in which the fiber-like members are disposed on the substrate.

A second aspect of the present invention is a photocatalytic apparatus, which includes a substrate member being made of substantially transparent material, a plurality of fiber-like members, each of the fiber-like members including photocatalytic material and disposed on the substrate member, and the photocatalytic material being composed of a plurality of photocatalytic particles (i.e. powders, small elements, small pieces).

Each of the fiber-like members is preferably composed of a core including the photocatalytic particles. Each fiber-like member may be composed of a core and a sheath including the photocatalytic particles, instead.

The substrate member is preferably composed of a transparent body including light diffusing particles. The transparent body may have a first surface, a second surface and at least one side.

Each of the fiber-like members may be composed of a fiber-like body, a first end and a second end. The first end may be fixed on the first surface and/or the second surface and/or the side, while the second end is free end.

In addition to the fiber-like members including photocatalytic material, another fiber-like members excluding photocatalytic material may be used, in which both fiber-like members are disposed on the substrate.

A third aspect of the present invention is a method for activating photocatalytic material, which includes the step of providing a photocatalytic apparatus composed of a substrate member; a plurality of fiber-like members disposed on the substrate member, each of the fiber-like members including the photocatalytic material, irradiating light capable of activating the photocatalytic material to the fiber-like members, oxidizing/reducing one or more substances being in contact with or approaching to the fiber-like members by means of photocatalizing oxidization/reduction reactions.

A fourth aspect of the present invention is a method for activating photocatalytic material, which includes the step of providing a photocatalytic apparatus composed of a substantially transparent substrate member; a plurality of fiber-like members disposed on the transparent substrate member, each of the fiber-like members including photocatalytic material, introducing light capable of activating the fiber-like members into an interior of the transparent substrate member, transmitting the light in said interior; irradiating said light output from said interior to said fiber-like members, and oxidizing/reducing one or more objects being in contact with the fiber-like members by means of photocatalizing oxidization/reduction reactions.

At least one light guiding member may be interposed between at least one light source and the transparent substrate member from the light source to the transparent substrate in order to guide the light.

The light guide member may be composed of a transparent rod capable of transmitting the light. Alternatively, the light guide member may be composed of an optical fiber or an optical cable capable of transmitting the light.

The transparent rod may have a transparent sheath with lower refractive index than that of the transparent rod. Alternatively, the transparent rod may have a light reflective sheath made of a light reflective metal.

Photocatalyst material used for the present invention is a kind of photo-activated or photocatalytic semiconductor, such as Titanium Dioxide ($TiO_2$), Tungsten Dioxide ($WO_2$), Zinc Oxide ($ZnO$), Tin Dioxide ($SnO_2$) and Zinc Sulfide ($ZnS$).

In the U.S. Pat. No. 4,526,570 to Nakagawa et al., a only sintered or coalesced semiconductor is used and the semiconductor does not disposed on brush bristles (i.e. fiber-like members), while in the present invention photocatalytic material is disposed on the fiber-like members. Further, in the present invention photocatalytic material is preferably composed of a plurality of photocatalytic particles, which are disposed on or in the fiber-like members.

It should be noted that the first aspect and the third aspect of the present invention have such advantages that an effective area of capable of coming in contact with or approaching to the photocatalyst material can be easily larger than the effective area of the prior art, because the photocatalytic material, preferably in a form of the plurality of photocatalytic particles, is disposed on the plurality of fiber-like members, and this structure also means that an effective area capable of receiving the light to activate the photocatalyst material can be easily larger than the prior art. Therefore, photocatalizing oxidation/reduction reactions can be remarkably accelerated by means of the first aspect and the third aspect of the present invention.

Further, it should be noted that the second aspect and the fourth aspect of the present invention have such advantages, in addition to the above-mentioned advantages, that the photocatalytic material can be irradiated effectively by the light output from the interior of the transparent substrate member, in which the light once inputs to the interior and outputs effectively in order to irradiate the photocatalytic fiber-like member after transmitting inside of the interior.

BRIEF DESCRIPTION OF THE DRAWINGS

A complete understanding of the present invention may be obtained from the following explanations, in connection with the accompanying drawings; in which.

DESCRIPTION OF THE PREFERRED EMBODIMENTS

Figure 1:
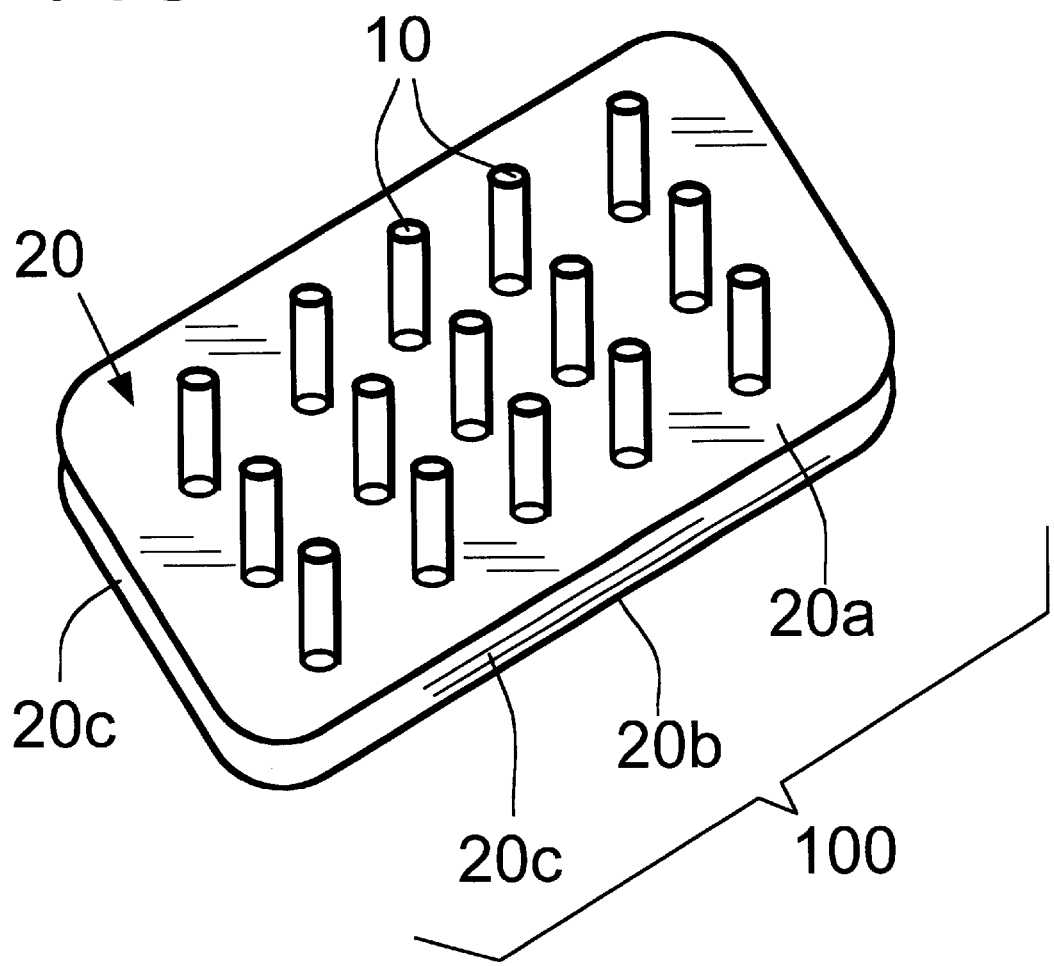
FIG. 1 illustrates a schematic enlarged perspective view of a cleaning head 100 in a cleaning tool 120, explaining a first preferred embodiment of the present invention.

The present invention will now be described in detail with reference to the drawings.

In the drawings, a relative dimension or size of each part or portion may be shown as somewhat different one to clarify an explanation of the present invention and the same parts or portions have the same reference numerals.

EMBODIMENT NO.1

Reference is made to FIG. 1, FIG. 2, FIG. 3, FIG. 4 and FIG. 5 showing a first preferred embodiment of the present invention.

Figure 2:
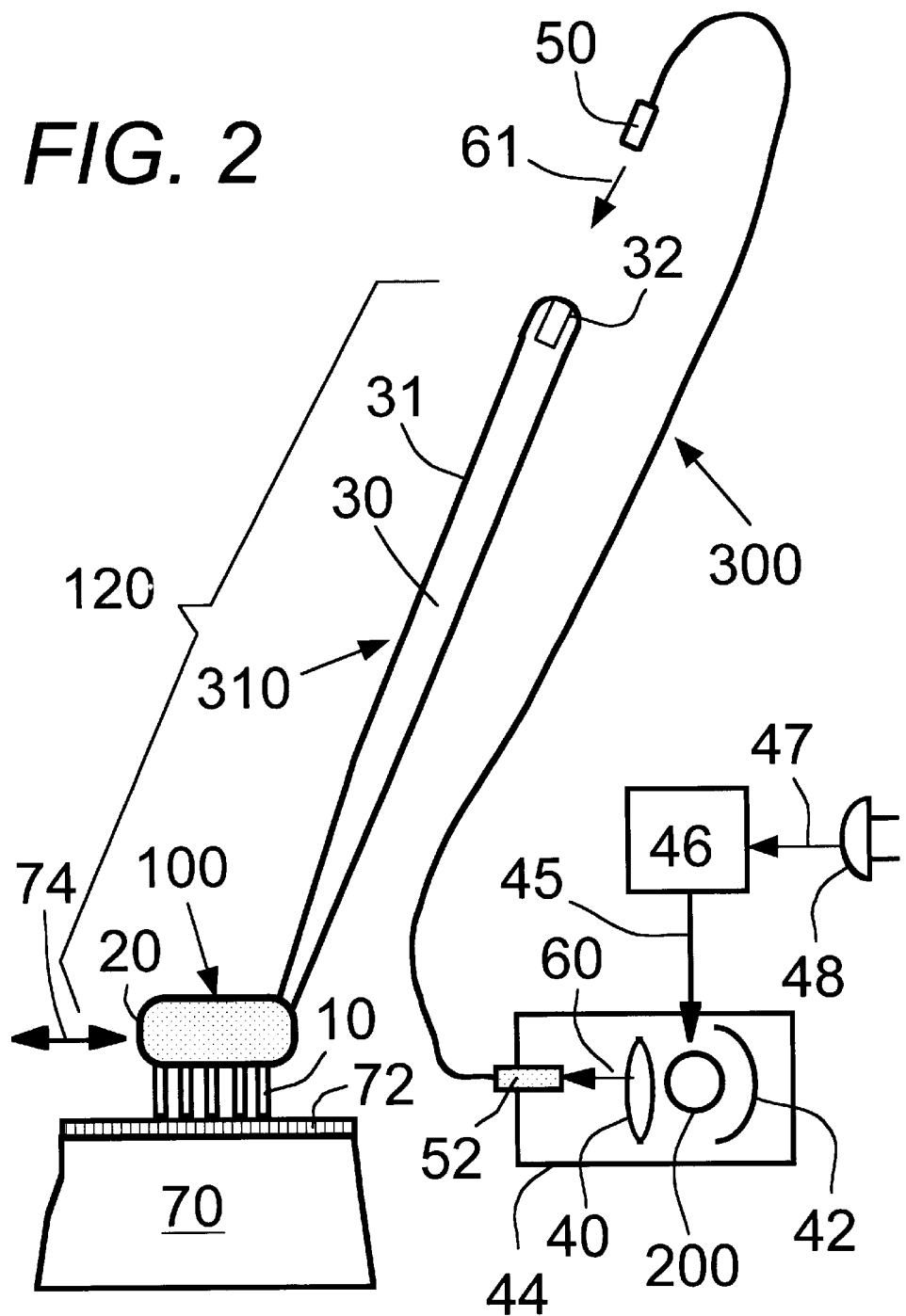
FIG. 2 illustrates a conceptual cross-sectional view of a cleaning apparatus, explaining the first preferred embodiment of the present invention.
Figure 3:
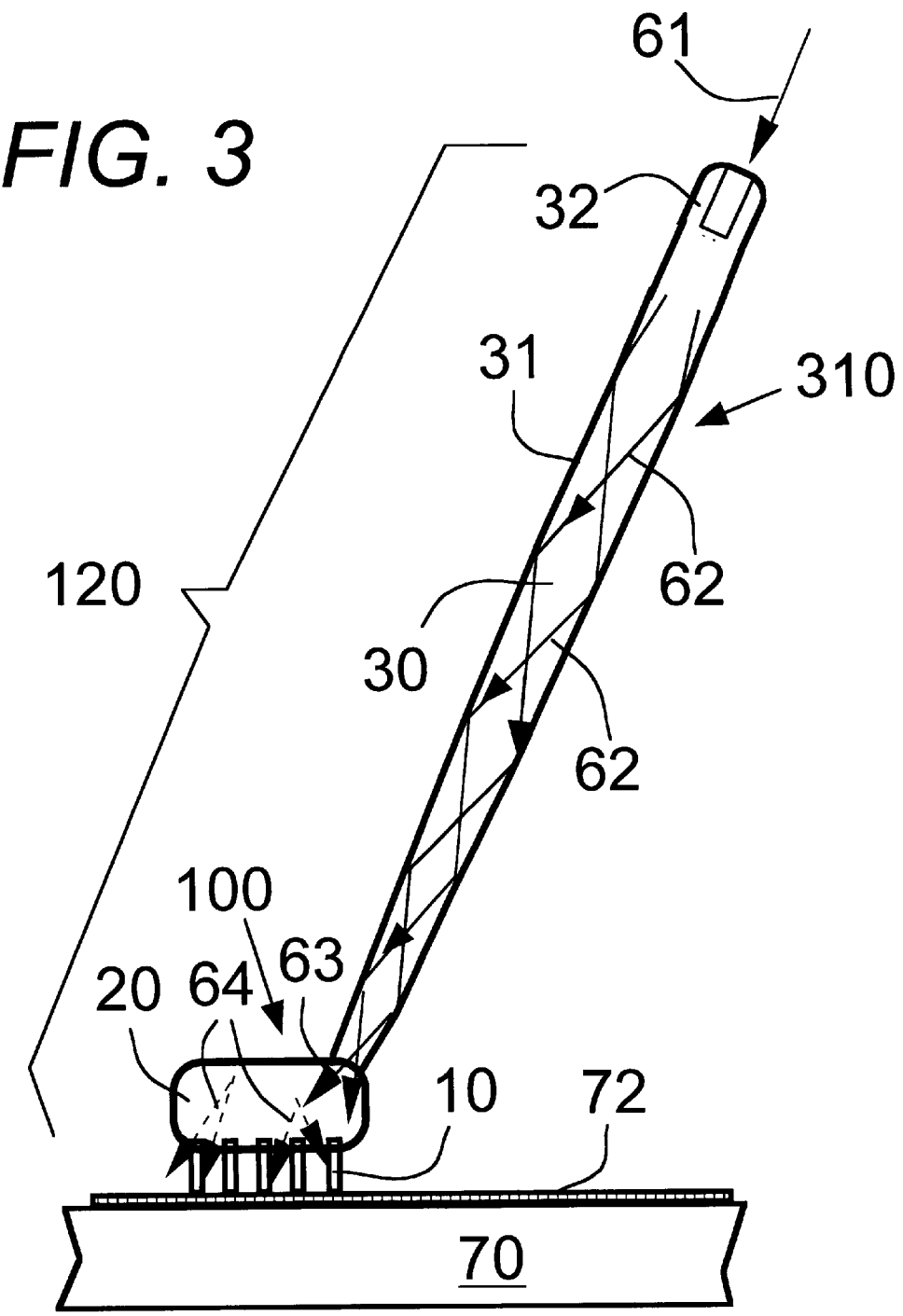
FIG. 3 illustrates a conceptual view of a light transmission passageway in cross-section of the cleaning tool 120 as shown in FIG. 2, explaining the first preferred embodiment of the present invention.
Figure 4:
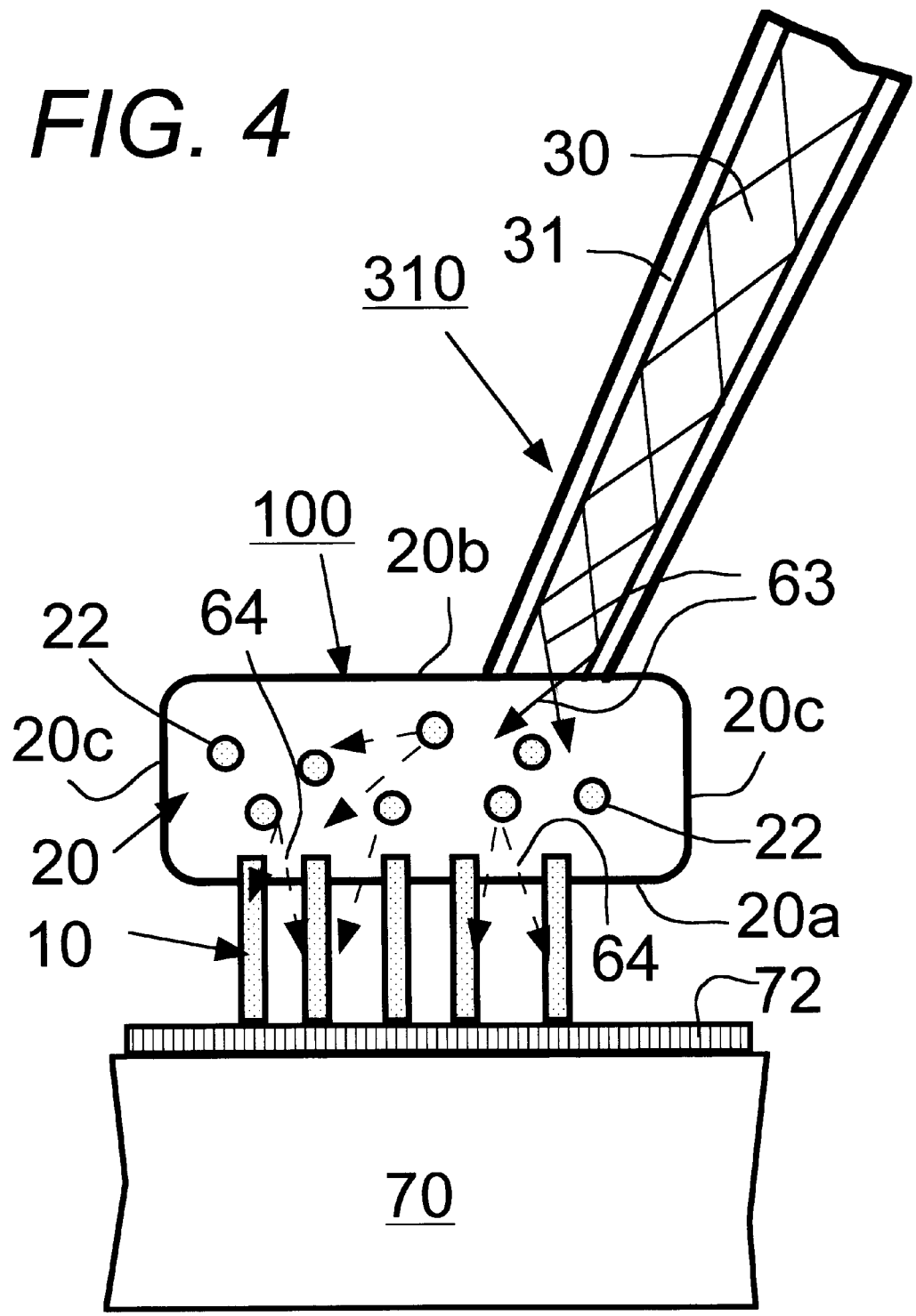
FIG. 4 illustrates a conceptual, partially omitted, and enlarged cross-sectional view of the cleaning tool 120 explaining a light transmission passageway in cross-section, explaining the first preferred embodiment of the present invention.

FIG. 1 shows an enlarged perspective view of a cleaning head 100 in a cleaning tool 120. FIG. 2 shows a cross-sectional view of a cleaning apparatus. FIG. 3 shows a light transmission passageway in cross-section of the cleaning tool 120 as shown in FIG. 2. FIG. 4 shows a partially omitted enlarged cross-sectional view of the cleaning tool 120 and a light transmission passageway. And FIG. 5 shows an enlarged cross-sectional view of a piece of brush among a group of brushes 10 in the cleaning head 100.

In FIG. 1, FIG. 2, FIG. 3 and FIG. 4, the cleaning apparatus (or cleaning device) 120 is roughly comprised of a cleaning tool 120, a light source 200 and an optical fiber or an optical fiber cable 300. The cleaning tool 120 is further comprised of a cleaning head 100 and a handle 310 with rod-like shape extending from the cleaning head 100.

The cleaning head 100 may further be comprised of a group of photocatalyst brushes (photocatalytic brushes) 10 and a transparent brush supporter. The group of photocatalyst brushes 10 may have multiple brushes, in which all or several brushes may include a photocatalyst. The transparent brush supporter 20 may fix ends of the photocatalyst brushes 10 and support them. It may be made of transparent material or transparent material embedding many light diffusing elements (particles) 22 (as shown in FIG. 4).

The handle 310 may be provided with a light inlet 32 (as shown in FIG. 2 and FIG. 3) which may be a hole, etc. in the most distant terminal of the handle 310 from the cleaning head 100. It may be comprised of a transparent rod 30 with high refractive index and a transparent layer 31 with low refractive index.

The transparent rod 30 may be coated or covered with the transparent layer 31 around the transparent rod 30. Since the transparent rod 30 is equivalent to a "core" of an optical fiber and the transparent layer 31 is equivalent to a "sheath" (or cladding) of the optical fiber functionally, the handle 310 is able to transmit most light rays effectively within the rod 30 with high transmission factor from the light inlet 32 to the cleaning head 100, according to a principle of the optical fiber. Alternatively, a light reflective layer such as aluminum or nickel may be used as a substitute for the transparent sheath (layer) 31 in order to obtain similar high transmission factor.

The brush supporter 20 may be made of transparent material capable of transmitting well ultraviolet rays, such as fused quarts, crystal glass as transparent inorganic materials and acrylic resin, polycarbonate resin, epoxy resin and transparent fluoric resin as transparent organic plastic materials.

For the light diffusing elements 22 in order to give the brush supporter 20 light diffusing characteristics, conventional white pigments may be used such particles as titanium oxide, aluminum, calcium carbonate and barium carbonate.

A reference numeral 70 indicates an substance to be cleaned (or a cleaned substance) such as a floor, a carpet and a wall in a building or a house, and a reference numeral 72 indicates a dirty component, which is contacted or adhered on a surface of the cleaned substance 70, as shown in FIG. 2, FIG. 3 and FIG. 4.

The light source 200 emits or generates short wavelength rays including ultraviolet (UV) rays. For the light source 200, various vacuum discharge lamps may be preferably used such as a germicidal lamp, a black light to cut visible light, a UV radiated fluorescent lamp, a halogen lamp and a conventional fluorescent lamp. A laser to emit coherent UV laser beam may also be used.

The germicidal lamp is a conventional low or high pressure mercury lamp using a UV transmissible glass tube such as transparent fused quarts, which emits UV light rays with short wavelength between the range from 250 nm to 280 nm (center wavelength; 253.7 nm) by discharge of mercury.

The black light is a kind of fluorescent lamp emitting blue color and UV light rays using a vacuum UV transmissible glass tube with a black filter to cut the UV light rays, or using a vacuum UV transmissible black filter glass tube to cut only the blue color light rays, which emits UV light rays with medium wavelength between the range from 380 nm to 300 nm by discharge of mercury.

The UV radiated fluorescent lamp may be used which uses a vacuum transparent glass tube without the black filter instead of the black light, which emits blue color light rays and also UV light rays with medium and long wavelength.

The halogen lamp is high-pressure mercury lamp adding metal halide inside the lamp tube, which emits UV light rays with medium and long wavelength.

Referring again to FIG. 2, a focus lens 40 and a reflector 42 positioned in rear of the focus lens 40 are installed. The light source 200, the focus lens 40 and the reflector 42 are housed in a light box (or a lamp house) 44. A commercial power is supplied from a power consent 48 to a light control circuit device 46 via an electric cable 47. The light control circuit device 46 controls a lighting of the light source 200. An optical fiber 300 may be comprised of a single number of optical fiber with a transparent core and a transparent sheath capable of transmitting UV light rays and a protective covering. Instead of the optical fiber, an optical fiber cable 300 may be used, which is comprised of multiple optical fibers capable of transmitting UV light rays and a protecting covering. The optical fiber 300 has a pair of optical fiber connectors 50 and 52 in both terminals. A light connector 50 and another light connector 52 of the optical fiber 300 are connected optically with the light inlet 32a of the handle 310 and with a light output of the lamp house 44, respectively.

The UV light rays 60 emitting from the light source 200 are collected at the focus lens 40 and are input at the light connector 52 of the optical fiber 300. The UV light rays 60 incident to the light connector 52 are transmitting in the optical fiber 300 to the light connector 50 and are introduced to the transparent handle 30 via the light inlet 32.

For transmissible materials of short wavelength rays for the optical fiber (core and cladding) 300, the handle 310 and the transparent brush supporter 20, such transparent inorganic materials may be used as Fused Quarts (including more than 99.9 weight % of $SiO_2$), Sapphire, Borosilicate glass (composing $SiO_2$; 75.3, $B_2O_3$; 13.8; ZnO; 1.4, $Al_2O_3$; 4.3, NaO; 5.0 weight %), etc. And also for the transmissible materials of the optical fiber, such transparent organic materials may be used as Acrylic base resin such as Polymethyl methacrylate (PMMA) (refractive index; N≈1.49), Polycarbonate (PC) (N≈1.59) resin, Polyethylene base resin such as Polyethylene terephthalate (PETP) (N≈1.58), Polystyrene (PS) (N≈1.59) and Fluoride base resin such as Polytetra fluoroethylene (PTFE), (N≈1.35), Epoxy resin (EP) (N≈1.55–1.61), etc. It is noted that the core of the optical fiber 300 (or the equivalent members 30 and 20) must be selected from material with comparatively high refractive index, while the cladding of the optical fiber 300 (or the equivalent members 31) must be selected from material with comparatively low refractive index. It is a matter of course that the core must be selected from material with high refractive index, while the sheath must be selected from material with low refractive index.

The UV transmitting optical fiber or cable 300 has been put into market. Such optical fiber capable of transmitting the light rays in ultraviolet region is available from famous cable manufacturers, such as Mitsubishi Cable Industries Ltd., Japan. For photocatalyst materials including in the photocatalyst brushes 10 of the cleaning head 100, photo-activated (i.e. photocatalytic) semiconductors may be used such as Titanium Dioxide; $TiO_2$ (photo activation wavelength; not more than 388 nm), Tungsten Dioxide; $WO_2$ (photo activation wavelength; not more than 388 nm), Zinc Oxide; ZnO photo activation wavelength; not more than 388 nm), Zinc Sulfide; ZnO photo activation wavelength; not more than 344 nm) and Tin Dioxide; $SnO_2$ photo activation wavelength; not more than 326 nm).

Especially the photo-activated Titanium Dioxide may be preferably applied for any fields, considering from that an activated power is very high, a life is long, durability is high and a safety or a harmless to a human body is certified, as it has been used for a long time safely for adding in cosmetics and foods.

Referring again to FIG. 3 and FIG. 4, as the UV transmissible handle 310 is set so that a refractive index N1 of the UV transmissible rod 30 is higher than a refractive index N2 of the UV transmissible sheath 31, the UV light rays 61 and 62 are transmitted effectively to the cleaning head 100 reflecting or refracting repeatedly. The UV light rays 63 are incident light rays in which the light rays 61 and 62 are transmitting to the UV transmissible brush supporter 20 of the cleaning head 100.

As shown in FIG. 4 (and FIG. 1 & FIG. 3), the cleaning head 100 may have many reflective elements (or reflective particles) 22 which are embedded in the UV transmissible brush supporter 20 in order to give UV light diffusing characteristics. Therefore, the UV light rays 63 incident to the brush supporter 20 are diffused at the reflective elements 22 to become diffusing (scattering) UV light rays 64 and the diffusing UV light rays 84 partially are outgoing outside from a front surface 20a of the brush supporter 20. The outgoing UV light rays 64 are incident to a group of brushes including photocatalyst (photocatalyst brushes) 10 and also incident to the dirty component 72.

The UV light rays 64 incident to the photocatalyst brushes 10 are forced to activate the photocatalyst component so that the dirty component 72 (shown in FIG. 2, FIG. 3 & FIG. 4) is oxidized and/or reduced by photocatalyst action, while the UV light rays 64 incident to the dirty component 72 sterilize directly the dirty component 72 by germicidal effect of the UV light rays 64.

A rear surface 20b and a side surface 20c of the brush supporter 20 excluding the front surface 20a may be preferably coated with light transmissible layer with low refractive index or light reflecting layer in order to obtain more amount of UV light output to the photocatalyst brushes 10.

FIG. 5 indicates an enlarged cross-section of a single brush or a fiber 10A or 10B of the group of photocatalyst brushes 10 in the cleaning head 100, according to a preferred embodiment NO.1.

Figure 5A:
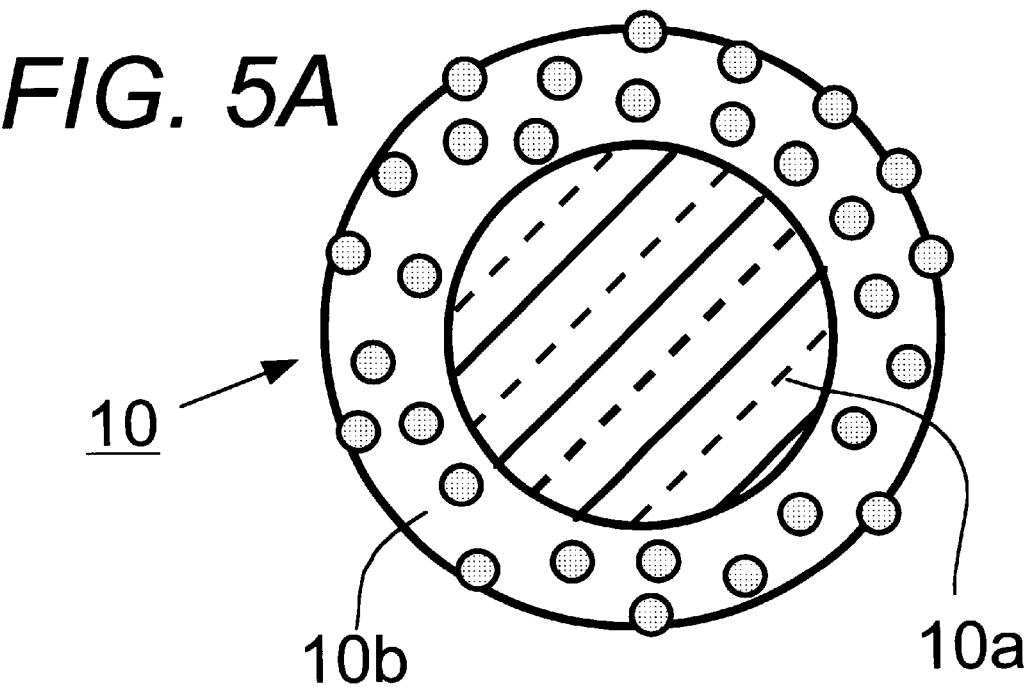
FIG. 5 illustrates an enlarged cross-sectional view of a piece of brush among a group of brushes 10 in the cleaning head 100, used in the first preferred embodiment of the present invention.
Figure 5B:
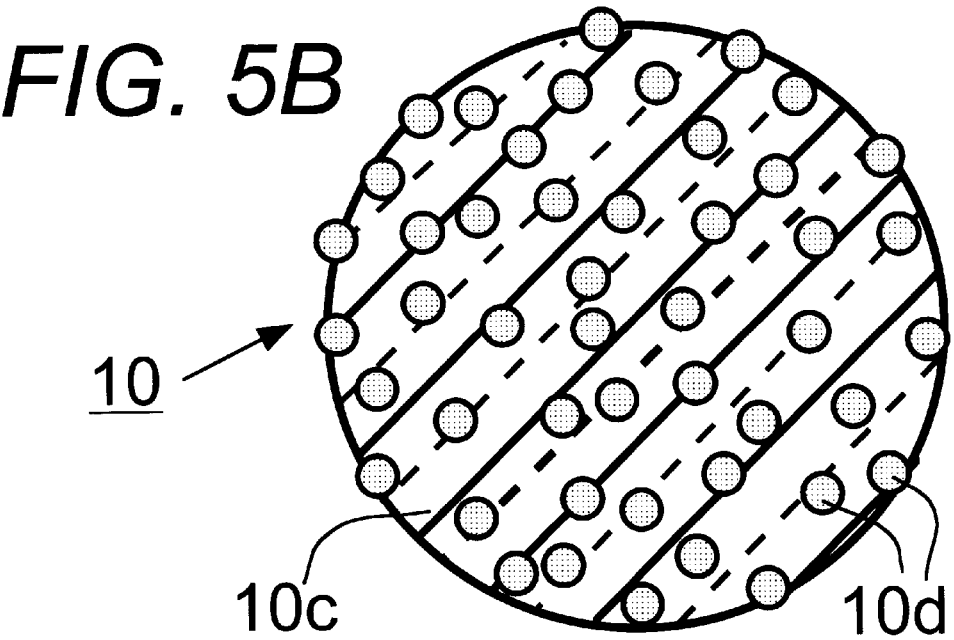

FIG. 5A indicates one type of the photocatalyst brush or fiber 10. It may be comprised of a composite fiber having a core 10a made of conventional artificial resin fiber (or metal wire) and a sheath including a photocatalyst 10b. The sheath is made of conventional artificial resin or rubber, in which many photocatalyst particles are embedded. FIG. 5B indicates another type of the photocatalyst brush or fiber 10 which may be comprised of a composite fiber having a core 10c made of a conventional artificial resin or rubber and many photocatalyst particles 10d embedded in the core 10c.

In more detail, in the case of FIG. 5A for example, the photocatalyst brush or fiber 10 may be comprised of a conventional artificial plastic fiber 10a (such as polyester, acrylic and polyimide i.e. nylon) or a conventional metal wire 10a (such as steel, stainless steel and titanium) and a sheath 10b coated around the fiber or wire 10a having an artificial plastic compound (such as polyamide; PA, polyethylene; PE, polypropylene; PP, polystyrene; PS, silicone rubber and chloroprene rubber) in which many photocatalyst particles or photocatalyst coated particles are embedded.

In the case of FIG. 5B, for example, the photocatalyst brush or fiber 10 may be comprised of a conventional artificial plastic or rubber fiber 10c (made of polymer or rubber such as polyester, acrylic, polyimide, polyamide; PA, polyethylene; PE, polypropylene; PP, polystyrene; PS, silicone rubber and chloroprene rubber) in which many photocatalyst particles 10d or photocatalyst coated particles 10d are embedded.

Referring to FIG. 2, FIG. 3 and FIG. 3, operation method for the cleaning apparatus of the preferred embodiment NO.1 is mentioned in sequence as follows:

At first, a power consent 48 is inserted into a receptacle of a commercial power supply to operate the light control circuit device 44 and to light on the UV light source 200; The optical connector 52 of the optical fiber or cable 300 is optically connected with an optical inlet of the lamp house 44 and another optical connector 50 of the optical fiber or cable 300 is optically connected with an optical inlet 32 of the handle 310 in the cleaning tool 120; The handle 310 of the cleaning tool 120 is gripped by a human hand or hands and the brushes 10 of the cleaning head 100 is moved to sweep and make a brushing back-and/or-forth as shown as an arrow mark 74 on the surface of the cleaned substance 72 such as floors, carpets, walls and human teeth; and The dirty component 72 as mentioned above can be easily dissolved, removed and cleaned up, because the dirty component 72 is contacted or closed to with the photocatalyst brushes 10 of the cleaning head 100, in which the photocatalyst brushes 10 is activated by radiation of the UV light rays 63 and 64 in order to oxidize and/or reduce the dirty component 72.

Simultaneously, the UV rays 63 incident to the transparent brush supporter 20 are going outside from a front surface of the brush supporter 20 and radiate or illuminate directly the dirty component 72 including such as bacteria, molds etc. on the cleaned substance 70 such as floors, carpets, walls etc., in addition to radiation to the brushes 10.

Therefore, when the germicidal lamp is preferably used for the UV light source 200, the dirty component 72 including such as bacteria, molds etc. can be sterilized by a sterilizing effect of the UV rays 63, 64, because it emits the UV rays between the range from 250 nm to 280 nm (center wavelength; 253.7 nm) exhibiting a strong sterilizing effect to bacteria, molds etc.

Accordingly, the dirty component 72 may be dissolved or sterilized indirectly by a photocatalyst effect according to activation of the photocatalyst and directly by the sterilizing effect according to radiation of the UV rays.

In all embodiments of the present invention, the same part or the same member has the same reference numeral. Therefore, in explaining various embodiments to be described below, different portions from the embodiment NO.1 already described are explained in detail and the portions already described are omitted as much as possible due to simplification of explanation.

EMBODIMENT NO.2

Figure 6:
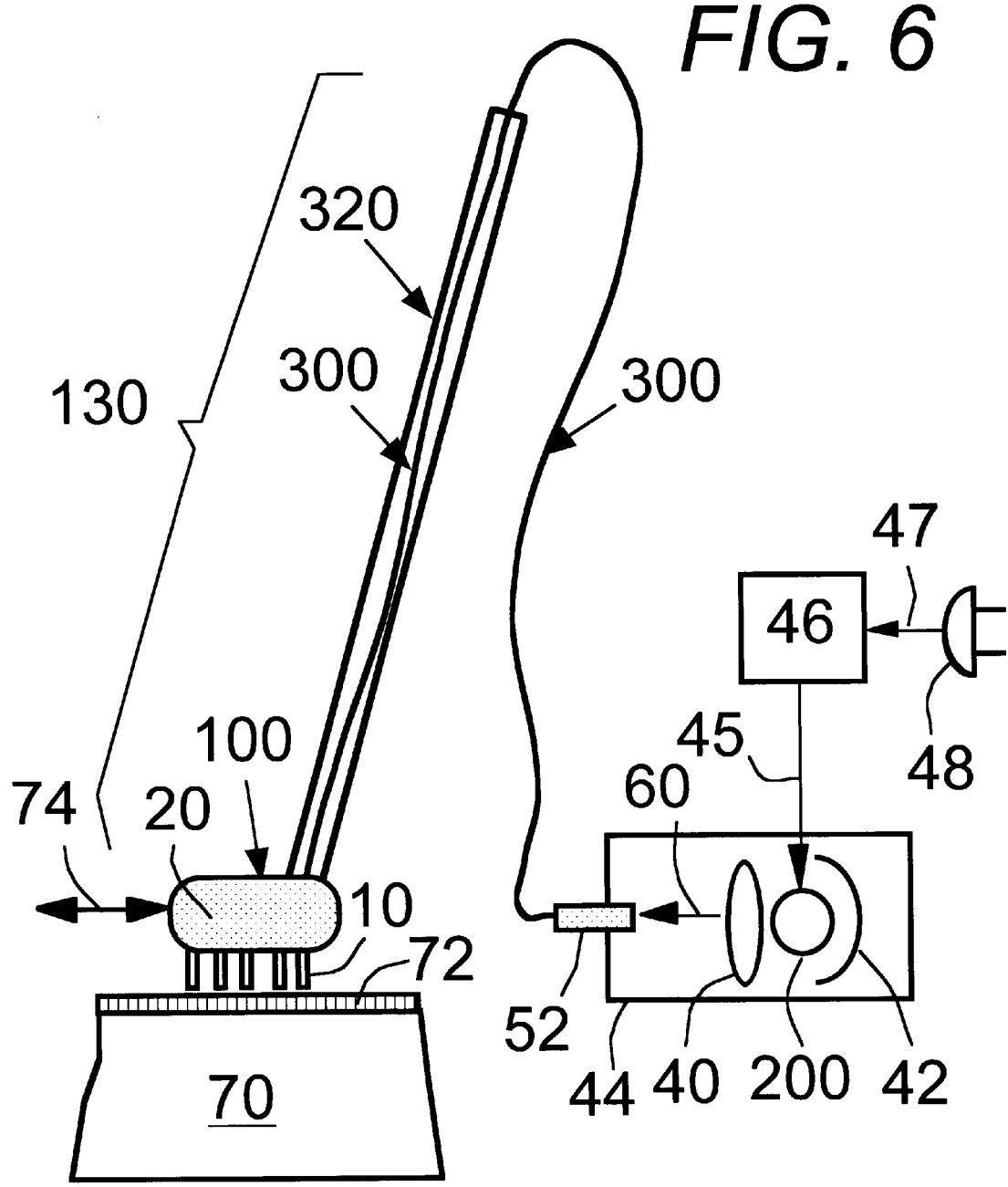
FIG. 6 illustrates a conceptual cross-sectional view of a cleaning apparatus, explaining a second preferred embodiment of the present invention.

FIG. 6 shows a second preferred embodiment of the present invention, in which a cleaning apparatus is roughly comprised of a cleaning tool 130, a light source 200, a light control circuit device 46 and an optical fiber 300.

The cleaning tool 130 is further comprised of a cleaning head 100 and a handle 320. The handle 320 is formed as a pipe of hollow tube and it is extended from the cleaning head 100 or it is connected with the cleaning head 100. A cleaning head 100 is further comprised of a group of brushes with a photocatalyst 10 (photocatalyst brushes) and a transparent brush supporter 20 by which the photocatalyst brushes 10 is fixed. Many light diffusing elements or particles 22 (shown in FIG. 4) may preferably be embedded in the transparent brush supporter 20.

In the embodiment NO.2, one terminal of the optical fiber 300 is connected to the cleaning head 100 by such as an optical fiber connector. The optical fiber 300 is passing inside through the handle of tube 320 and is going outside and is finally connected to a light output part of a lamp house 44 by a detachable optical or light connector 52 of the optical fiber 300.

UV light rays 60 emitting from the light source 200 are gathered by a focus lens 40 and, are input to the optical fiber 300 through the optical connector 52 and are arrived in the cleaning head 100 through the optical fiber 300. In the embodiment NO.2, efficient UV rays transmission is obtained with minimum transmission loss, due to use of UV transmissible optical fiber as mentioned in the embodiment NO.1.

EMBODIMENT NO.3

Figure 7:
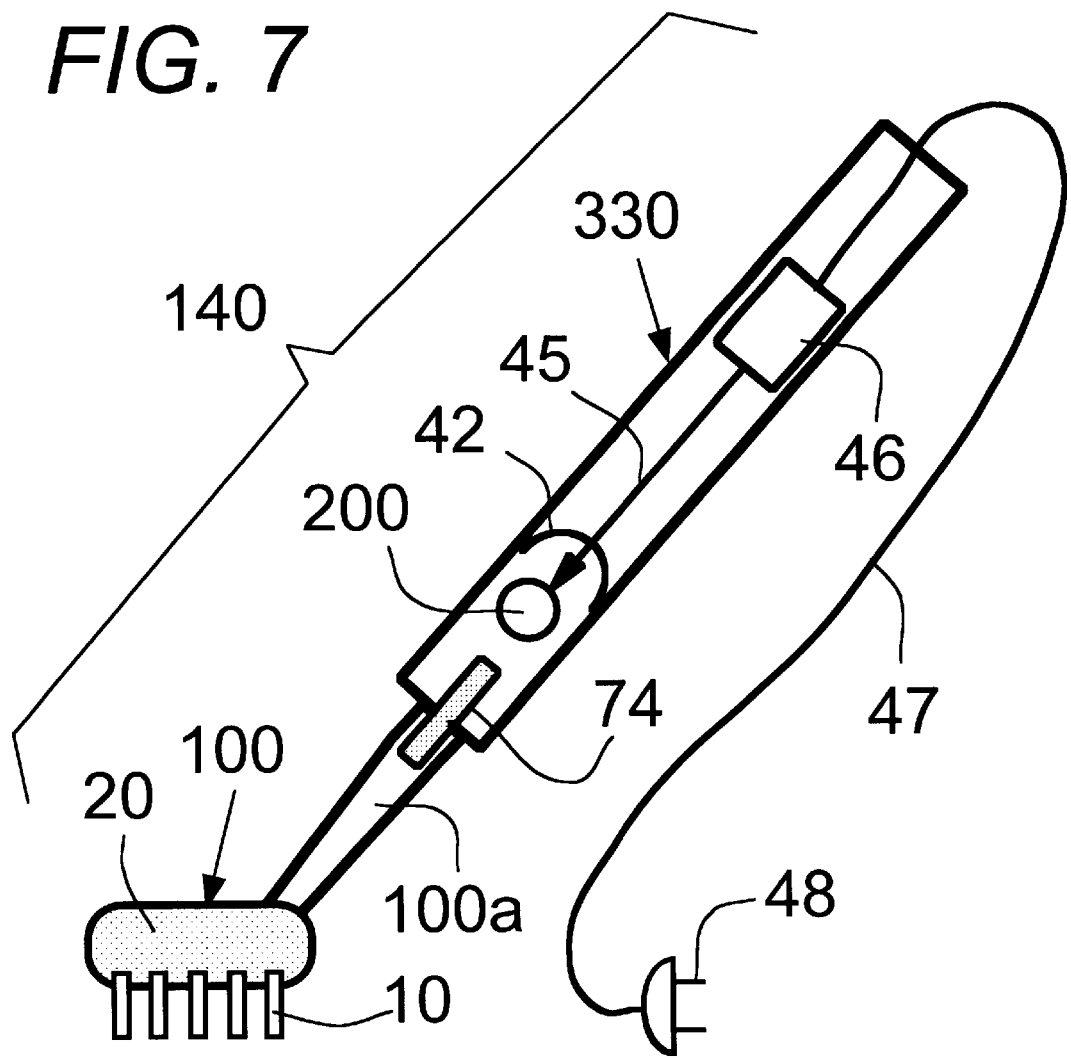
FIG. 7 illustrates a conceptual cross-sectional view of a cleaning apparatus, explaining a third preferred embodiment of the present invention.

FIG. 7 shows a third preferred embodiment of the present invention, in which a cleaning apparatus is roughly comprised of a cleaning tool 140, a light source 200 and a light control circuit device 46.

The cleaning tool 140 is further comprised of a cleaning head 100, a transparent neck 100a of a part of the cleaning head 100 and a handle 330. The handle 330 is formed as a pipe of hollow tube and it is extended from the transparent neck 100a, which is enlarged as taper shape in cross-section toward the handle 330.

A cleaning head 100 is further comprised of a group of brushes with a photocatalyst 10 (photocatalyst brushes) and a transparent brush supporter 20 by which the photocatalyst brushes 10 is fixed. Many light diffusing elements or particles 22 (shown in FIG. 4) may preferably be embedded in the transparent brush supporter 20.

In the embodiment NO.3, a cleaning tool 140, a light source 200, a light control circuit device 46 and a reflector 42 are housed in a hollow portion of the handle 330. Light rays emitting from the light source 200 are optically connected and mechanically fixed with the transparent neck 100a via an optical connector 74.

The light control circuit device 46 is electrically connected with an electric cord 47, an electric power supply is fed to the light control circuit device 46 via a power consent 48 and the light source 200 is lit on by an power output of the light control circuit device 46. The UV light rays emitting from the light source 200 are gathered by the reflector 42 and introduced into a transparent brush supporter of the cleaning head 100 through the optical connector 74 and the transparent neck 100a. In the embodiment NO.3, the cleaning apparatus becomes very compact, as most components of the cleaning apparatus are accommodated in the cleaning tool 140.

EMBODIMENT NO.4

Figure 8:
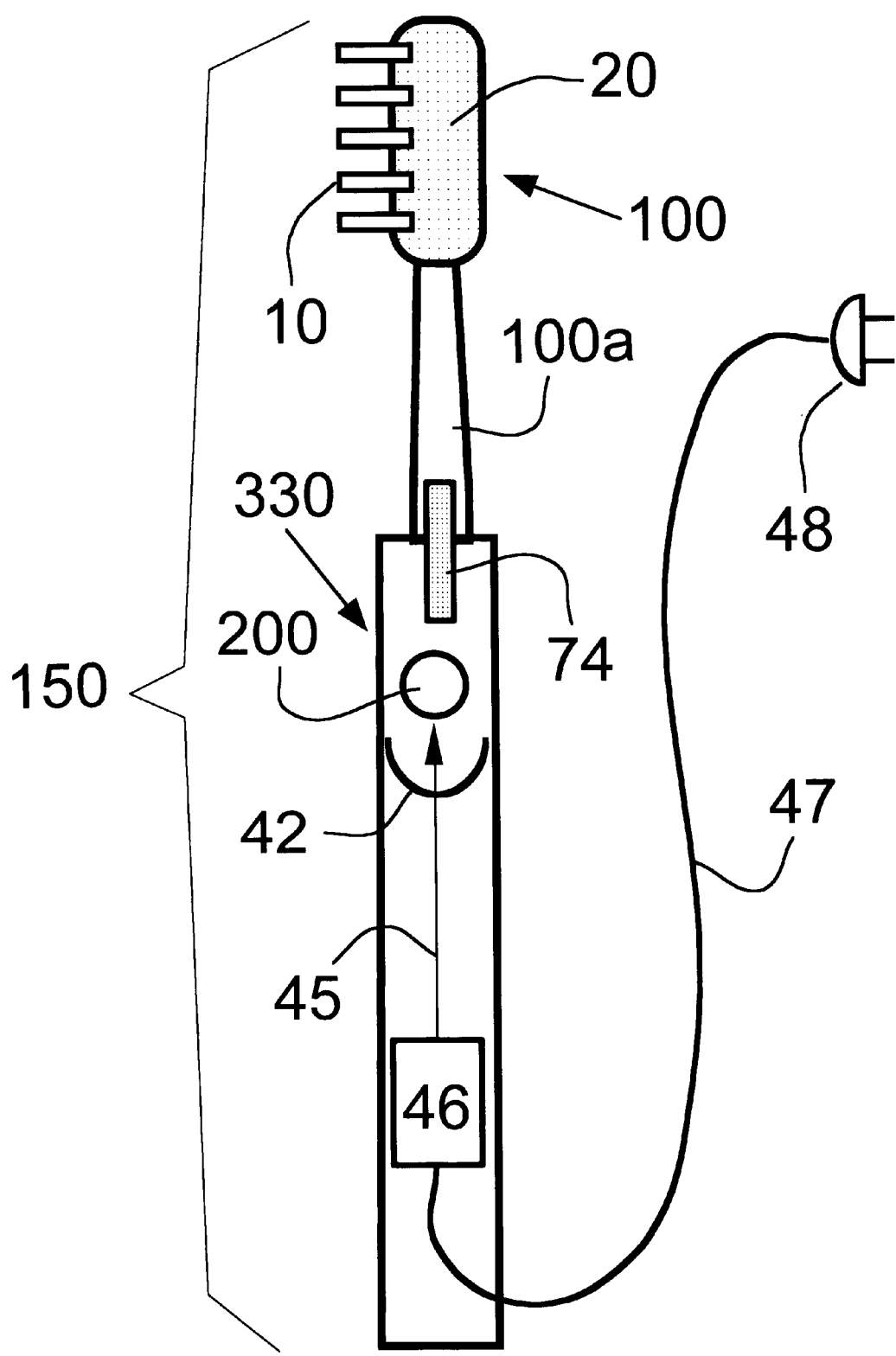
FIG. 8 illustrates a conceptual cross-sectional view of a cleaning apparatus 150, explaining a fourth preferred embodiment of the present invention.
Figure 9:
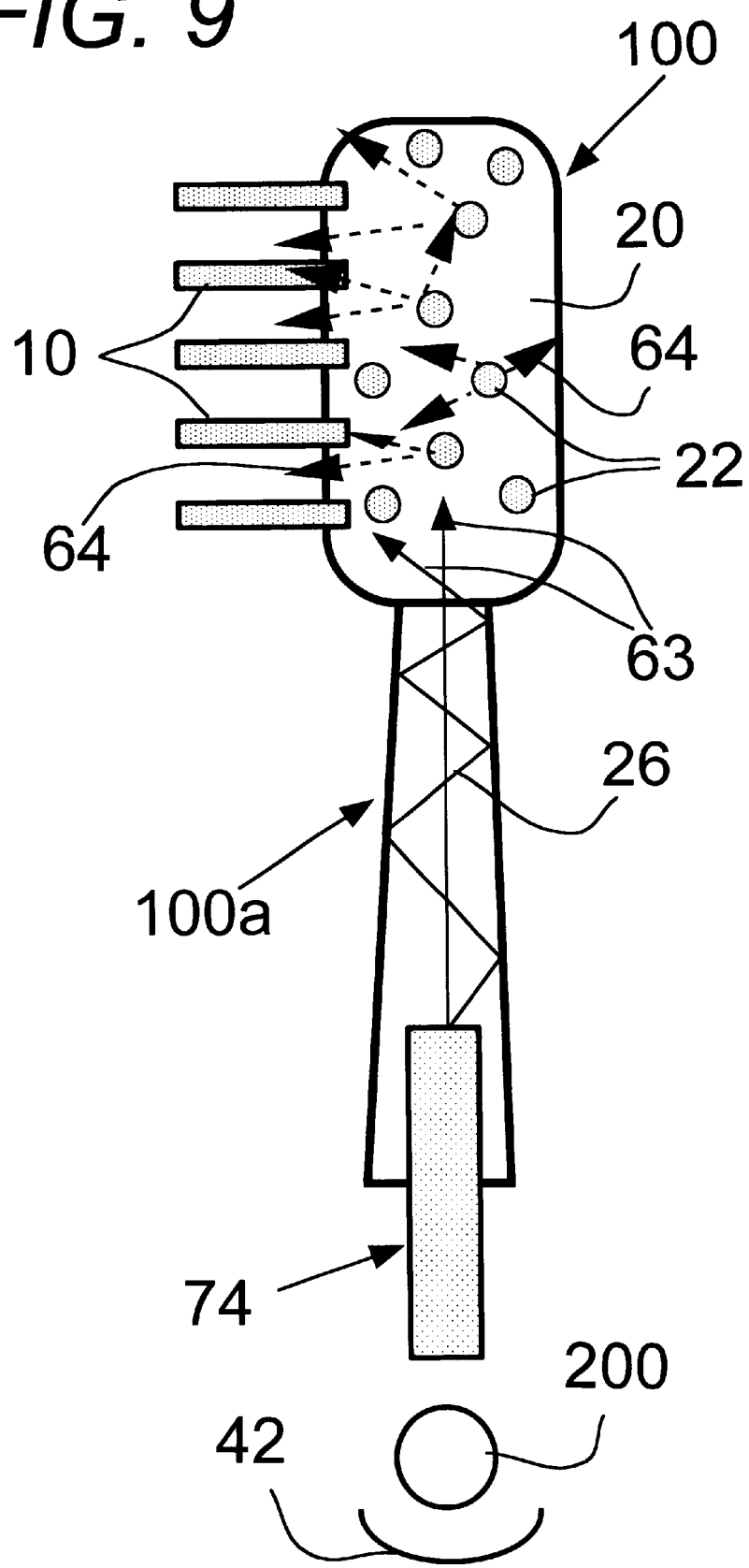
FIG. 9 illustrates a conceptual, partially omitted, enlarged cross-sectional view of the cleaning apparatus 150 and also a light transmission passageway as shown in FIG. 8, explaining the fourth preferred embodiment of the present invention.

FIG. 8 and FIG. 9 show a third preferred embodiment of the present invention. A cleaning apparatus is roughly comprised of a cleaning tool 150, a light source 200 and a light control circuit device 46, similar to the embodiment NO.3. The cleaning tool 150 is further comprised of a cleaning head 100, a transparent neck 100a of a part of the cleaning head 100 and a handle 330. The handle 330 is formed as a pipe of hollow tube, in which the light source 200, the light control circuit device 46 and a reflector are accommodated inside the hollow tube. UV light rays generating from the light source 200 are collected by a reflector 42 and are incident to the transparent neck 100a of taper shape. The light rays arrived at the he transparent neck 100a are transmitting directly to a transparent brush support 20 of the head 100 or transmitting by repeating multiple reflection 26 to the brush support 20. Incident light rays 63 input into the brush supporter 20 are striking to at least one of many light diffusing particles 22 embedded in the brush supporter 20 and become diffusing light rays 64. The diffusing light rays 64 radiate the photocatalyst brushes 10 by which the brushes are activated to be oxidized and/or reduced.

EMBODIMENT NO.5

Figure 10:
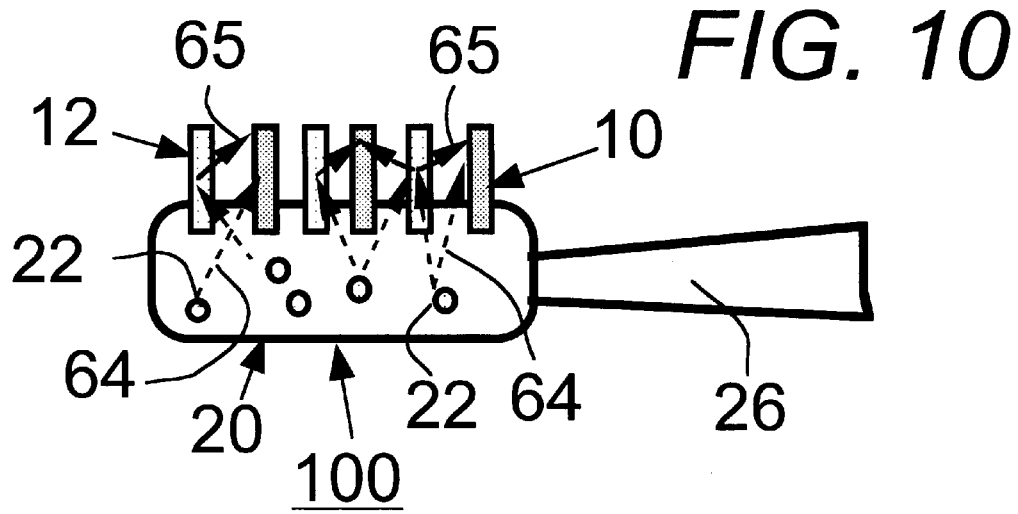
FIG. 10 illustrates a conceptual, partially omitted, and enlarged cross-sectional view of a cleaning head 100, explaining a fifth preferred embodiment of the present invention.

In FIG. 10 showing a fifth preferred embodiment of the present invention, only blush portion of a cleaning head 100 is varied from other embodiments. The cleaning head 100 is comprised of a transparent brush supporter 20, many light diffusing particles 22 embedded in the supporter 20 and the two kinds of brushes consisting of photocatalyst brushes with photocatalyst 10 and transparent brushes without photocatalyst 12. In the embodiment NO.5, light diffusing rays 64 radiate directly the photocatalyst brushes 10 or radiate indirectly the photocatalyst brushes 10 through the transparent brushes without photocatalyst 12.

EMBODIMENT NO.6

Figure 11:
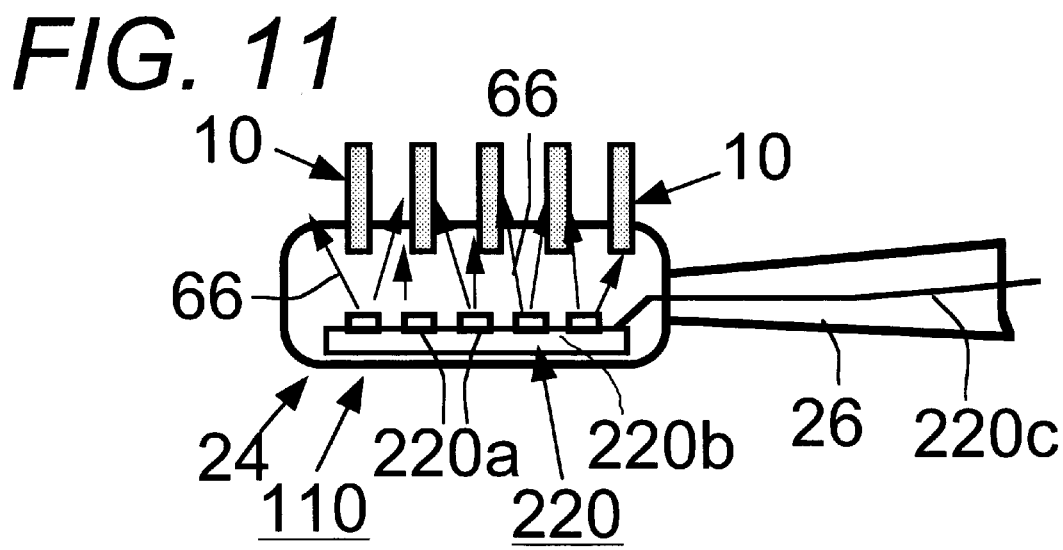
FIG. 11 illustrates a conceptual, partially omitted, enlarged cross-sectional view of a cleaning head 110, explaining a seventh preferred embodiment of the present invention.

In FIG. 11 showing a sixth preferred embodiment of the present invention, a cleaning head 110 is comprised of a photocatalyst brushes 10 and a brush supporter 24 and a semiconductor light source 220 having a printed wire board 220b and a light emitting diode (LED) or diodes 220a capable of emitting short wavelength rays. The semiconductor light source 220 is embedded in the brush supporter 24 made of transparent resin and an electric power is supplied from lead wires 220c to the light source 220. In this case, very small size of cleaning apparatus is obtained for use on a tooth brushing, etc.

EMBODIMENT NO.7

Figure 12:
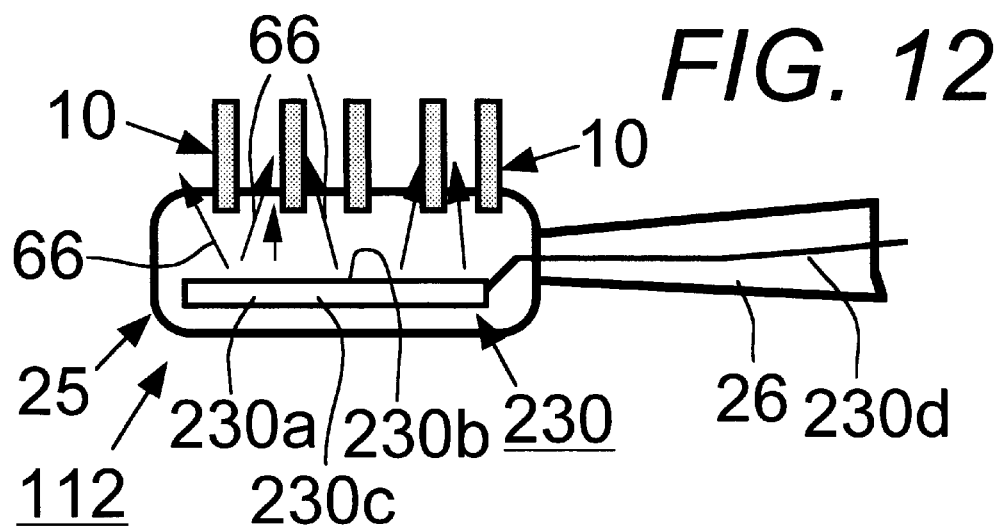
FIG. 12 illustrates a conceptual, partially omitted, and enlarged cross-sectional view of a cleaning head 112, explaining an eighth preferred embodiment of the present invention.

In FIG. 12 showing a seventh preferred embodiment of the present invention, a cleaning head 112 is comprised of photocatalyst brushes 10 and a brush supporter 25 and a semiconductor light source 230, in which the semiconductor light source 230 is composed of a light emitting layer 230c sandwiched by an electrode layer 230a and a transparent electrode layer 230a capable of emitting short wavelength rays (The light source 230 is called as "EL" i.e. an electorluminescent device). The EL 230 is embedded in the brush supporter 24 made of transparent resin. The EL 230 is lit on, when an electric power is supplied from lead wires 220d. In this case, very small size of a cleaning apparatus is obtained for use on a tooth brushing, etc.

EMBODIMENT NO.8

Figure 13:
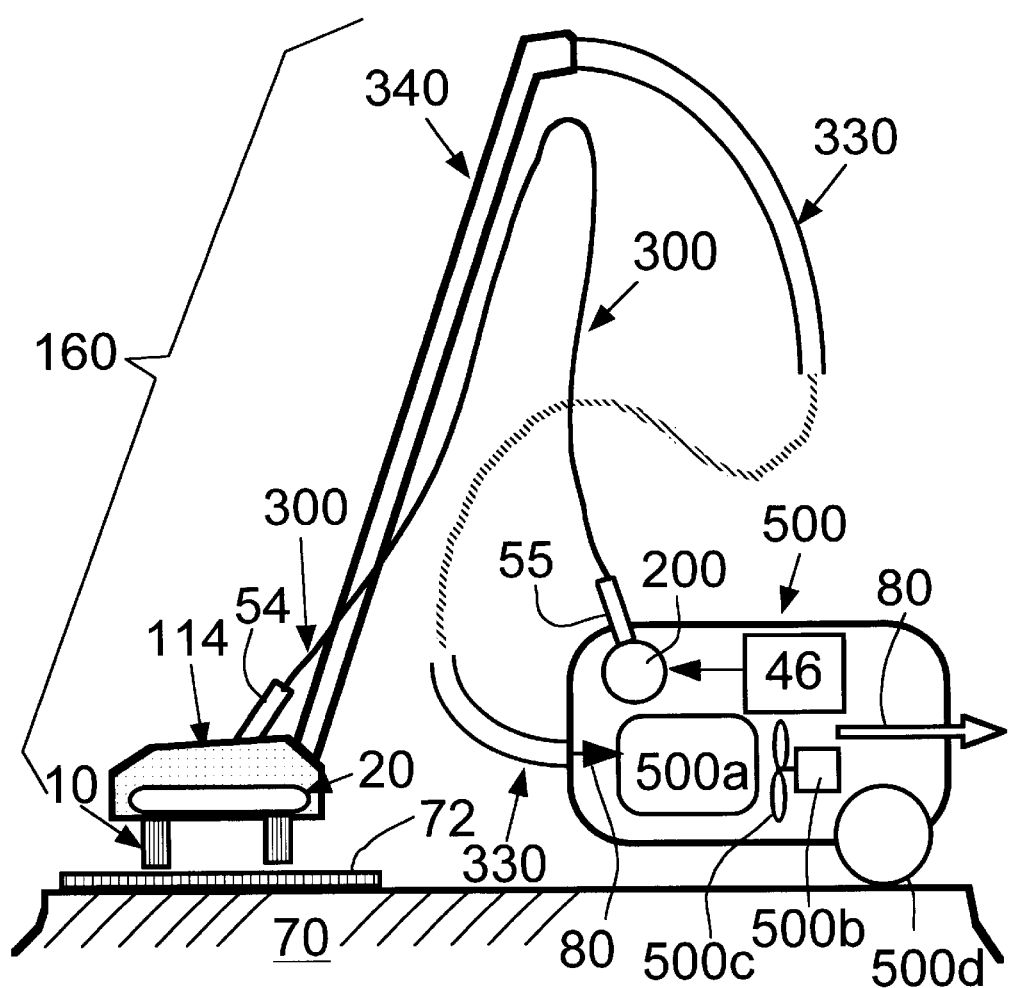
FIG. 13 illustrates a conceptual cross-sectional view of a cleaning apparatus; explaining a tenth preferred embodiment of the present invention, in which the invention is applied to a vacuum cleaner.
Figure 14:
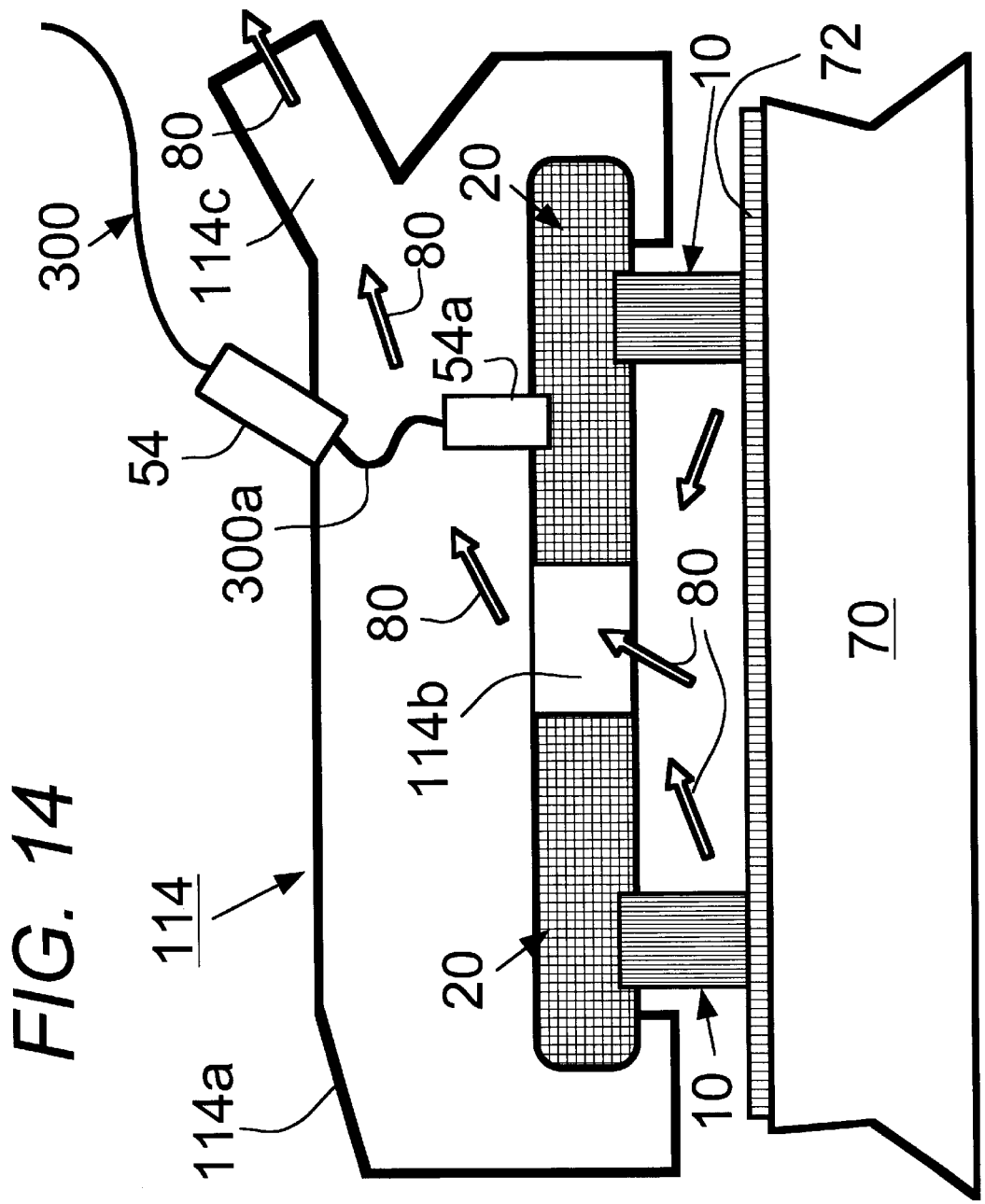
FIG. 14 illustrates a schematic, partially omitted, enlarged cross-sectional view of neighborhood of a cleaning head 114 as shown in FIG. 13, explaining the tenth preferred embodiment of the present invention.

Referring to FIG. 13 and FIG. 14, an eighth preferred embodiment of the invention is explained, in which a cleaning apparatus of the invention is applied to a vacuum cleaner.

As shown in FIG. 13, the vacuum cleaner is roughly comprised of a cleaning tool 160, a main cleaner body 500, a flexible hose 330 and an optical fiber cable (or optical fiber) 300. The cleaning tool 160 is further comprised of a cleaning head (having a nozzle, a hood and a suction inlet) 114 and a tube type handle (or wand) 340. The cleaner body 500 in the body casing accommodates a motor 500b, a fan 500c rotating by the motor 500b, a dust keeping means (i.e. a dust bag, or a dust case) 500a, a light source 200 to emit short wavelength rays, a light control circuit device 46 and wheels (or casters) 500d for the cleaner body 500 to move easily on an substance to be cleaned such as floors and carpets. The cleaning head 114 accommodates a transparent brush supporter 20 and a group of brushes 10 with photocatalyst. The flexible hose 330 is connected with a terminal of the handle (or wand) 340 in a terminal of the hose 330 and a vacuum inlet of the cleaner body 500 in another terminal of the hose 330.

The optical fiber cable 300 capable of transmitting short wavelength rays is connected optically with the light source 200 via an optical connector 55 at a terminal of the optical fiber cable 300 and the cleaning head 114 via another optical connector 54 at another terminal of the optical fiber cable 300. Accordingly, short wavelength rays emitted from the light source 200 housed in the cleaner body is transmitted to the transparent brush supporter 20 housed in the cleaning head 114 via the optical fiber cable 300 and radiate the photocatalyst brushes 20 to activate photocatalyst.

Therefore, when the fan 500c is rotating according to rotation of the motor 500b, an air pressure in a forward of the fan 500c is decreased and a dirty component 72 on the floor or the carpet is forced to sucked together with an air from the cleaning head 114 and the dirty component 72 is gathered inside the dust bag or dust case 500a through the hollow of the handle 340, the flexible hose 330. Arrows 80 indicate airflows.

In FIG. 14 showing an enlarged detail of the cleaning head 114, the cleaning head 114 is comprised of the head case 114a, the transparent brush supporter 20 having the group of photocatalyst brushes 10 and a suction hole 114b, a connecting pipe 114c to connect the handle 340 (shown in FIG. 13) a detachable optical connector 54a to connect between the brush supporter 20 and an optical fiber 300a. The cleaning head 114 accommodates the brush supporter 20 with photocatalyst brushes 10 in the head case 114a and it is constructed to keep air tightness, when the photocatalyst brushes 10 contact or approach to the floor 70 (or carpet, etc.). The photocatalyst brushes 10 are the fibers including many photocatalyst particles 10 and they are fixed in a bottom of the brush supporter 20 as shown in FIG. 5.

Referring again to FIG. 13 and FIG. 14, the optical fiber cable 300 extended from the optical fiber connector 55 in one end is connected to the optical fiber connector 54 in another end fixed at the head case 114. The short optical fiber 300 is optically connected between the optical fiber connector 54 and the optical fiber connector 54 a.

Therefore, the dirty component 72 contacted or adhered on the surface of the cleaned substance 70, for example, a floor is forced to remove from the surface by contacting (or sweeping, brushing) of the photocatalyst brushes 10 and moves to an upper portion of the head case 114a via the suction inlet 114b of the brush supporter 20 and goes out from the connecting pipe 114c according to the airflow 80. Short wavelength rays transmitted in the cleaning head 114 are transmitted to the transparent brush supporter 20 and radiate the photocatalyst brushes 10. Since the photocatalyst brushes 10 are activated by radiation of the short wavelength rays, the dirty component 72 contacted or approached with the activated photocatalyst brushes 10 is oxidized or reduced so as to clean up.

EMBODIMENT NO.9

Figure 15:
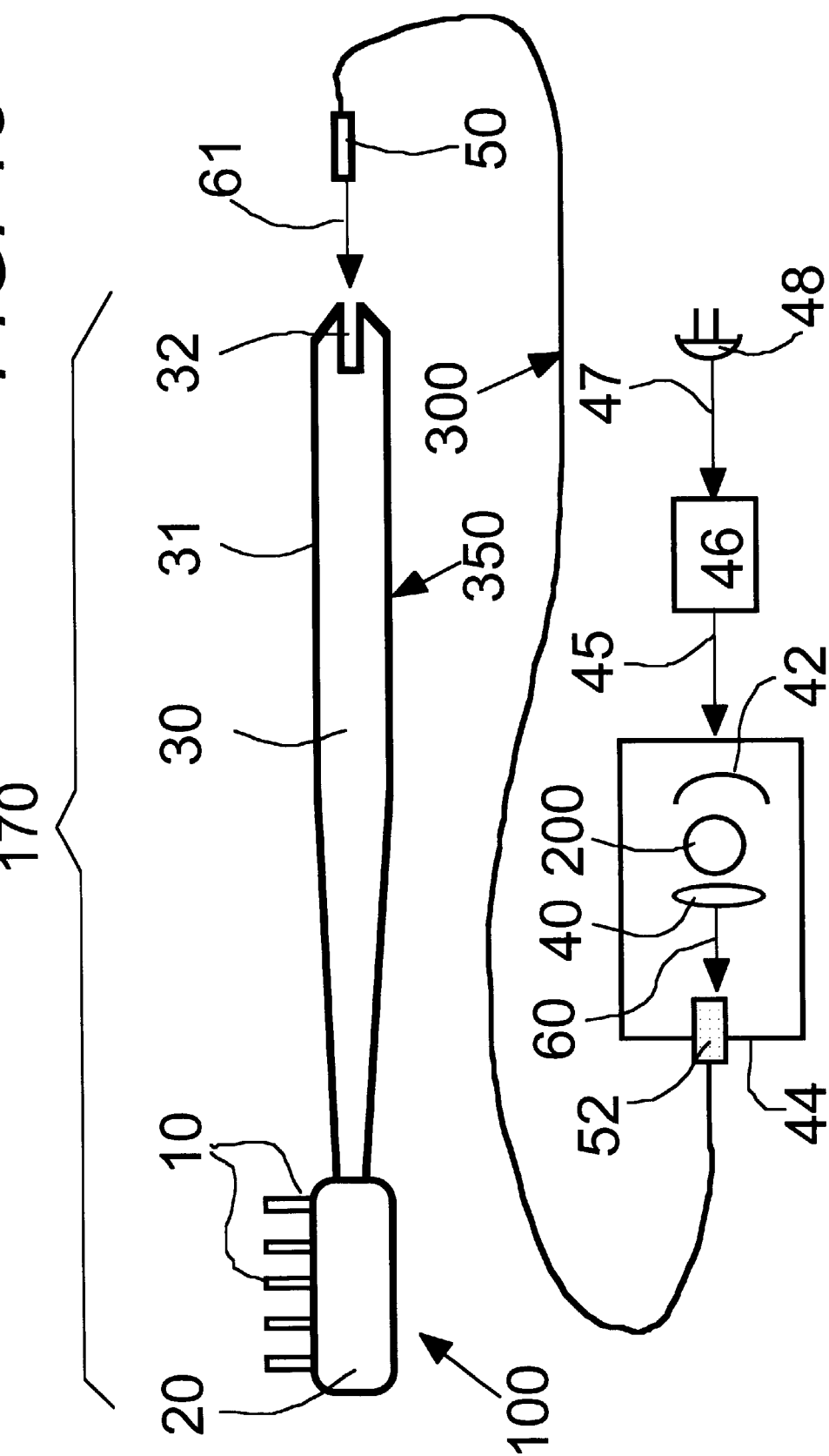
FIG. 15 illustrates a conceptual cross-sectional view, explaining an eleventh preferred embodiment of the present invention, in which the invention may be applied to a dental cleaner.

FIG. 15 shows a ninth preferred embodiment of the invention, in which a cleaning apparatus of the invention may be applied to a dental cleaner or tooth brushing apparatus.

As shown in FIG. 15, the dental cleaner is roughly comprised of a teeth brushing tool 170, a light source 200 to emit short wavelength rays (UV rays, etc.), a light control circuit device 46 and an optical fiber 300 to transmit UV light rays. The tooth brushing tool 170 is further comprised of a cleaning head 100 having a transparent brush supporter 20 to fix brushes 10 with photocatalyst and a handle 350 having a transparent rod 30 of taper shape in cross-section to transmit UV light rays, a light reflecting sheath 31 to reflect UV light rays and a light inlet 32. The optical fiber 300 has an optical connector 50 in an end and another optical connector 52 in another end. The optical fiber 300 is connected detachably to the light inlet 32 of the transparent rod 30 in an end via the optical connector 50 and to a light incident inlet of a lamp house 44 via the optical connector 52.

Short wavelength rays 60 emitted from the light source 200 is incident to the optical fiber 300 via a lens 40 and the optical connector 52 and they are transmitting in the optical fiber 300 and they become output short wavelength rays 61. The output rays 61 are incident to the transparent handle 30 of the tooth-brushing tool 350 via the optical connector 50 and they 61 are transmitting in the transparent handle 30 and are transmitting to the cleaning head 100. The short wavelength rays 61 incident to the cleaning head 100 are radiating the photocatalyst brushes 10, in which a photocatalyst component is activated.

When a teeth brushing is done by using the tooth brushing tool 170 to surface of teeth, gums, and between teeth, etc. such dirty components inside a mouse are easily dissolved and removed according to photocatalyst action as residue or garbage of food, bacteria, molds, plaque, scale and nicotine/tar due to smoking.

EMBODIMENT NO.10

Figure 16:
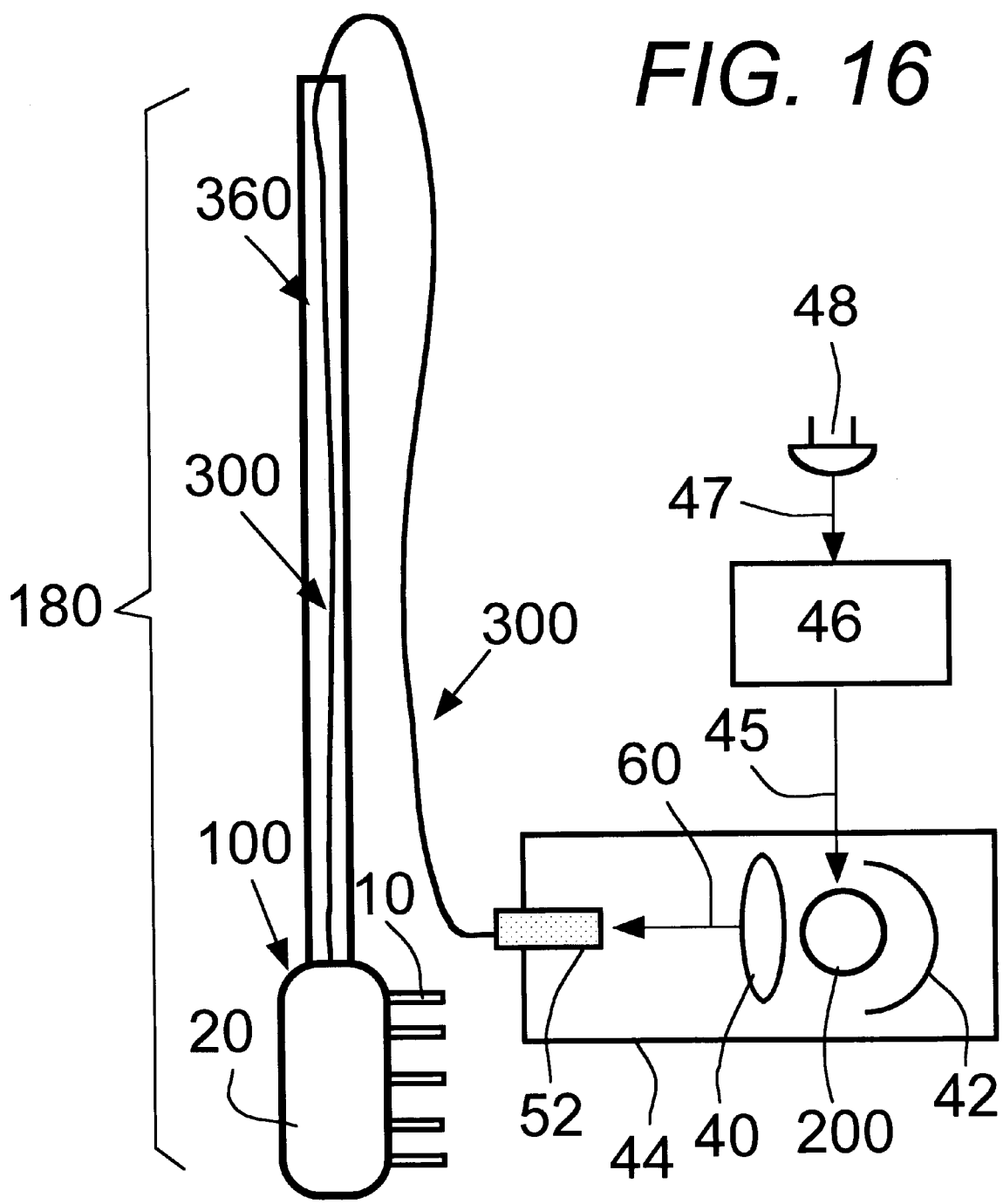
FIG. 16 illustrates a conceptual cross-sectional view, explaining a twelfth preferred embodiment of the present invention, in which the invention may be applied to a dental cleaner.

FIG. 16 shows a tenth preferred embodiment of the invention, in which a cleaning apparatus of the invention may be applied to a dental cleaner or tooth brushing apparatus, similarly to the embodiment NO.9 previously explained.

As shown in FIG. 16, the dental cleaner is roughly comprised of a teeth brushing tool 180, a light source 200 to emit short wavelength rays (UV rays, etc.), a light control circuit device 46 and an optical fiber 300 to transmit UV light rays. The teeth brushing tool 180 is further comprised of a cleaning head 100 having a transparent brush supporter 20 to fix brushes 10 with photocatalyst and a handle 360 of tube connected or jointed to the cleaning head 100 at an end. The optical fiber 300 at an end is connected with the cleaning head 100, it is passing through an inside of the tube 360 (handle), it is going outside and finally at another end it is connected with a light output inlet of a lamp house 44 by a detachable optical connector 52.

Since an optical fiber cable includes multiple optical fibers, an optical cable may be used instead of an optical fiber, or vice versa in the above-mentioned embodiments.

This is a division of U.S. patent application Ser. No. 09/161,013, filed on Sep. 25,1998, and issued on Aug. 1, 2000 as U.S. Pat. No. 6,094,767. The prior foreign application of the U.S. patent application Ser. No. 09/161,013 is Japanese Patent application No. H08-103131, filed on Mar. 21, 1996, laid open on Sep. 30, 1997 as Publication of unexamined patent application (i.e. Laying-open of application) No. 253595/1997. Therefore, the U.S Patent document and the Publication of unexamined patent application are hereby incorporated herein by reference.

While the preferred embodiments of the present invention have been disclosed, it is to be understood that various changes, modifications, combinations or equivalents will be apparent to those skilled in the related art without departing from the spirit of the present invention.

Therefore, the scope of the present invention is to be determined solely by the appended claims.

What is claimed is:

1. A photocatalyst apparatus, comprising:

a substrate;

a plurality of photocatalytic fibers, each of the photocatalytic fibers having a core or a sheath covering the core and a plurality of photocatalytic particles dispersed therein; and wherein the photocatalytic fibers are disposed on/in the substrate.

2. The photocatalyst apparatus according to claim 1: further comprising at least one light reflective layer disposed on the substrate; wherein the light reflective layer comprises (a) a light reflective metallic material or (b) a transparent material with a lower refractive index than a refractive index of the substrate.

3. The photocatalyst apparatus according to claim 1: wherein the photocatalytic fibers are fixed to/on the substrate at each end of the photocatalytic fibers.

4. The photocatalyst apparatus according to claim 1: wherein the substrate comprises a substantially transparent member; wherein the substrate receives light from an exterior thereof to introduce light to an interior thereof so as to transmit light therein; and wherein the photocatalytic fibers are irradiated by light output from the substrate.

5. The photocatalyst apparatus according to claim 1: further comprising at least one light source in communication with the photocatalytic fibers; and wherein the light source is disposed (a) at a vicinity of the substrate, (b) at an interior of the substrate so to be embedded therein or (c) at a position separated from the substrate in such a way that at least one light guide member and/or optical fiber are interposed between the light source and the substrate.

6. The photocatalyst apparatus according to claim 1: further comprising at least one light source to emit UV rays having a wavelength in the range from 250 nm to 280 nm for exhibiting a sterilizing effect to bacteria and/or molds and for activating the photocatalytic fibers.

7. The photocatalyst apparatus according to claim 1: further comprising a plurality of non-photocatalytic fibers excluding a photocatalyst, disposed on the substrate.

8. The photocatalyst apparatus according to claim 1: wherein the photocatalyst apparatus is a dental cleaner or a toothbrush.

9. A photocatalyst apparatus, comprising:

a substrate having a substantially transparent member and a plurality of light diffusing particles dispersed therein; and a plurality of photocatalytic fibers disposed on/in the substrate, each of the photocatalytic fibers containing a photocatalyst disposed therein/thereon.

10. The photocatalyst apparatus according to claim 9: wherein each of the light diffusing particles comprises a pigment.

11. The photocatalyst apparatus according to claim 9: wherein each of the light diffusing particles comprise a pigment selected from the group consisting of titanium oxide, aluminum, calcium carbonate, barium carbonate and a combination thereof.

12. The photocatalyst apparatus according to claim 9: wherein the photocatalyst comprises a plurality of photocatalytic particles.

13. The photocatalyst apparatus according to claim 9: wherein each of the photocatalytic fibers comprises a core or a sheath covering the core and the photocatalyst having a plurality of photocatalytic particles; and wherein the photocatalytic particles are dispersed in the core or the sheath.

14. The photocatalyst apparatus according to claim 9: wherein the photocatalytic fibers are fixed to/on the substrate at each end of the photocatalytic fibers.

15. The photocatalyst apparatus according to claim 9: further comprising at least one light reflective layer disposed on the substrate; wherein the light reflective layer comprises (a) a light reflective metallic material or (b) a transparent material with a lower refractive index than a refractive index of the substrate.

16. The photocatalyst apparatus according to claim 9: wherein the substrate receives light from an exterior thereof to introduce light to an interior thereof so as to transmit light therein, and wherein the photocatalytic fibers are irradiated by light output from the substrate.

17. The photocatalyst apparatus according to claim 9: further comprising at least one light source in communication with the photocatalytic fibers, and wherein the light source is disposed (a) at a vicinity of the substrate, (b) at an interior of the substrate so to be embedded therein or (c) at a position separated from the substrate in such a way that at least one light guide member and/or optical fiber are interposed between the light source and the substrate.

18. The photocatalyst apparatus according to claim 9: further comprising at least one light source to emit UV rays having a wavelength in the range from 250 nm to 280 nm for exhibiting a sterilizing effect to bacteria and/or molds and for activating the photocatalytic fibers.

19. The photocatalyst apparatus according to claim 9: further comprising a plurality of non-photocatalytic fibers excluding a photocatalyst, disposed on the substrate.

20. The photocatalyst apparatus according to claim 9: wherein the photocatalyst apparatus is a dental cleaner or a toothbrush.

21. A cleaner for cleaning floors, carpets and/or walls, the cleaner comprising:

a cleaning head including a plurality of photocatalytic brushes containing a photocatalyst disposed thereon/therein;

at least one light source in communication with the photocatalyst; and wherein each of the photocatalytic brushes comprises a core or a sheath covering the core and the photocatalyst having a plurality of photocatalytic particles dispersed in the core or the sheath.

22. The cleaner according to claim 21: wherein the cleaning head includes a substrate to support the photocatalytic brushes.

23. The cleaner according to claim 21: wherein the cleaning head includes a substantially transparent substrate to support the photocatalytic brushes and a plurality of light diffusing particles dispersed in the substrate.

24. The cleaner according to claim 21: wherein the cleaning head includes a substantially transparent substrate to support the photocatalytic brushes and a plurality of light diffusing particles dispersed in the substrate; and wherein each of the light diffusing particles comprises a pigment.

25. The cleaner according to claim 21: wherein the cleaning head includes a substantially transparent substrate to support the photocatalytic brushes and a plurality of light diffusing particles dispersed in the substrate; and wherein each of the light diffusing particles comprises a pigment selected from the group consisting of titanium oxide, aluminum, calcium carbonate, barium carbonate and a combination thereof.

26. The cleaner according to claim 21: wherein the cleaning head includes a substantially transparent substrate to support the photocatalytic brushes and at least one light reflecting layer disposed on the substrate; and wherein the light reflective layer comprising (a) a light reflective metallic material or (b) a transparent material with a lower refractive index than a refractive index of the substrate.

27. The cleaner according to claim 21: further comprising at least one light source in communication with the photocatalytic brushes; and wherein the light source is disposed (a) at a vicinity of the cleaning head, (b) at an interior of the cleaning head so to be embedded therein or (c) at a position separated from the cleaning head in such a way that at least one light guide member and/or optical fiber are interposed between the light source and the cleaning head.

28. The cleaner according to claim 21: wherein the light source emits UV rays having a wavelength in the range from 250 nm to 280 nm for exhibiting a sterilizing effect to bacteria and/or molds and for activating the photocatalytic brushes.

29. The cleaner according to claim 21: further comprising a plurality of non-photocatalytic brushes to exclude a photocatalyst, disposed on the substrate.

30. The cleaner according to claim 21: wherein the cleaner is a vacuum cleaner including a motor, a fan, dust keeping means and the cleaning head.

* * * * *